United States Patent
Pennino

(10) Patent No.: US 7,842,255 B2
(45) Date of Patent: Nov. 30, 2010

(54) CARBAMATE CONDENSATION METHOD AND UNIT FOR CARRYING OUT SUCH A METHOD

(75) Inventor: Lorenzo Pennino, Lugano (CH)

(73) Assignee: Urea Casale S.A. (CH)

( * ) Notice: Subject to any disclaimer, the term of this patent is extended or adjusted under 35 U.S.C. 154(b) by 448 days.

(21) Appl. No.: 11/850,222

(22) Filed: Sep. 5, 2007

(65) Prior Publication Data

US 2008/0085229 A1    Apr. 10, 2008

Related U.S. Application Data

(62) Division of application No. 10/937,952, filed on Sep. 10, 2004, now Pat. No. 7,279,599.

(30) Foreign Application Priority Data

Sep. 19, 2003   (EP) .................................. 03021279

(51) Int. Cl.
*B01J 19/00* (2006.01)
*B01J 8/04* (2006.01)
*C10J 1/00* (2006.01)
*F28D 7/00* (2006.01)

(52) U.S. Cl. ..................... 422/198; 422/201; 422/202; 422/205; 422/211; 261/75; 261/100; 165/81; 165/140; 165/159; 165/160; 165/161; 165/162

(58) Field of Classification Search ................. 422/198, 422/196, 197, 201, 202, 205, 211; 261/75, 261/100; 165/81, 140, 159, 160, 161, 162

See application file for complete search history.

(56) References Cited

U.S. PATENT DOCUMENTS

| 2,385,200 | A | 9/1945 | Friedel |
| 3,268,435 | A | 8/1966 | Sellin |
| 4,792,436 | A | 12/1988 | Tsai |
| 6,284,922 | B1 | 9/2001 | Pagani et al. |
| 6,702,992 | B2 * | 3/2004 | Pagani et al. ................. 422/189 |
| 7,091,379 | B2 | 8/2006 | Zardi |
| 2002/0041838 | A1 * | 4/2002 | Rizzi ........................... 422/197 |
| 2004/0028578 | A1 * | 2/2004 | Zardi ........................... 422/188 |

FOREIGN PATENT DOCUMENTS

EP   1 036 787 A1   9/2000

\* cited by examiner

*Primary Examiner*—Walter D Griffin
*Assistant Examiner*—Huy-Tram Nguyen
(74) *Attorney, Agent, or Firm*—Akerman Senterfitt

(57) ABSTRACT

Method for carbamate condensation of a carbon dioxide/ammonia gaseous phase in a liquid phase in a condensation unit of the so-called submerged type comprising a heat exchange tube bundle having a predetermined number of tubes intended for carbamate condensation, wherein the gaseous phase and the liquid phase are fed contemporaneously and independently to each of the tubes intended for condensation.

12 Claims, 4 Drawing Sheets

CARBAMATE CONDENSATION METHOD AND UNIT FOR CARRYING OUT SUCH A METHOD

FIELD OF APPLICATION

The present invention relates to a method for carbamate condensation in a unit of the so-called submerged type, used in a plant for the production of synthesis urea from gaseous carbon dioxide and liquid ammonia.

The present invention also relates to a carbamate condensation unit for carrying out the above method

PRIOR ART

In order to produce urea, the reactants, i.e. carbon dioxide and ammonia, are fed partially condensed in form of carbamate in a synthesis reactor, wherein the condensation of carbamate, an intermediate product of the synthesis, is carried out to an almost complete extent. Only a portion of the carbamate is then converted into urea in the reactor itself, by virtue of the chemical balances that characterize this conversion.

The remaining portion of unconverted carbamate, together with the unreacted ammonia, is then forced out of the reactor and at least partially recovered, by stripping, for example with $CO_2$, in form of gaseous ammonia and carbon dioxide by per se known processes.

These gaseous compounds must then be partially condensed, thus obtaining their conversion into liquid carbamate that is then recycled to the synthesis reactor.

As known, in a plant for urea production, it is required to convert through condensation into carbamate part of the reactants and of the intermediate products that, unconverted into urea in the synthesis reactor, are recovered downstream thereof in form of gaseous ammonia and carbon dioxide.

In order to satisfy the aforesaid requirement, in EP-A-1 036 787 a condensation unit of the so-called submerged type has been proposed, comprising a cylindrical shell inside which is supported a tube bundle, wherein the tubes are straight and in heat exchange relationship with a suitable coolant.

In the tube bundle, with the tubes full of liquid (submerged), ammonia and carbon dioxide condensation takes place, together with their reaction to form carbamate.

Although advantageous as far as some aspects thereof are concerned, the condensation unit exhibits a remarkable drawback that will be described hereinbelow.

In fact, it has been found out that, contrary to the expected design operation, only a minor portion of the tubes of the tube bundle intended for condensation are indeed used for the conversion into carbamate of the gaseous compounds flowing from a lower end to an upper end thereof. The remaining major portion of such tubes of the tube bundle are on the contrary flown by the liquid phase only and in part used for the recycle of a portion of the condensed gaseous compounds from the upper end to the lower end of the tube bundle. In other words, it has been found out that the gaseous compounds flow within the tube bundle throughout preferential paths of heterogeneous reactant concentration defined within a very limited number of tubes.

Since, given a tube bundle of predetermined size, the yield is strictly bound to the only part thereof intended for the condensation (i.e. flown by the gaseous compounds), the presence of a relevant portion of tubes intended for condensation flown by the liquid phase only, drastically reduce the condensation yield of the condenser. Moreover, it also negatively affects the natural circulation of the liquid phase inside the condenser thus decreasing the efficiency of the apparatus.

SUMMARY OF THE INVENTION

The technical problem underlying the present invention is that of providing a method for carbamate condensation in a unit of the so-called submerged type, wherein the efficiency and the condensation yield are remarkably increased with respect to the teaching of the prior art.

According to the present invention, this problem is solved by a method for carbamate condensation of a carbon dioxide/ammonia gaseous phase in a liquid phase in a condensation unit of the so-called submerged type comprising a heat exchange tube bundle having a predetermined number of tubes intended for carbamate condensation, characterized by the step of:
feeding, contemporaneously and independently, said gaseous phase and said liquid phase within each of said tubes intended for condensation.

Thanks to the present invention, it is possible to effectively use all tubes of the tube bundle intended for condensation to convert into carbamate the gaseous compounds. In fact, the step of feeding separately and independently the gaseous phase and the liquid phase, respectively, to each single tube intended for condensation, allows advantageously to uniformly and homogenously distributing the gaseous compounds within all of such tubes.

In this respect, it should also be noted that with the present method, the condensation reaction is carried out within each of the tubes intended for condensation at substantially the same operating conditions, to all advantage of the heat exchange coefficient and of the condensation yield.

As the tubes of the tube bundle intended for condensation are indeed used to carry out the condensation, the method of the present invention allows advantageously to obtain an efficiency and a condensation yield of the condensation unit which substantially corresponds to the design one.

Further features and advantages of the present invention will appear more clearly from the following non-limiting description of an embodiment thereof, made with reference to the attached drawings.

DETAILED DESCRIPTION OF THE DRAWINGS

Figure 1:
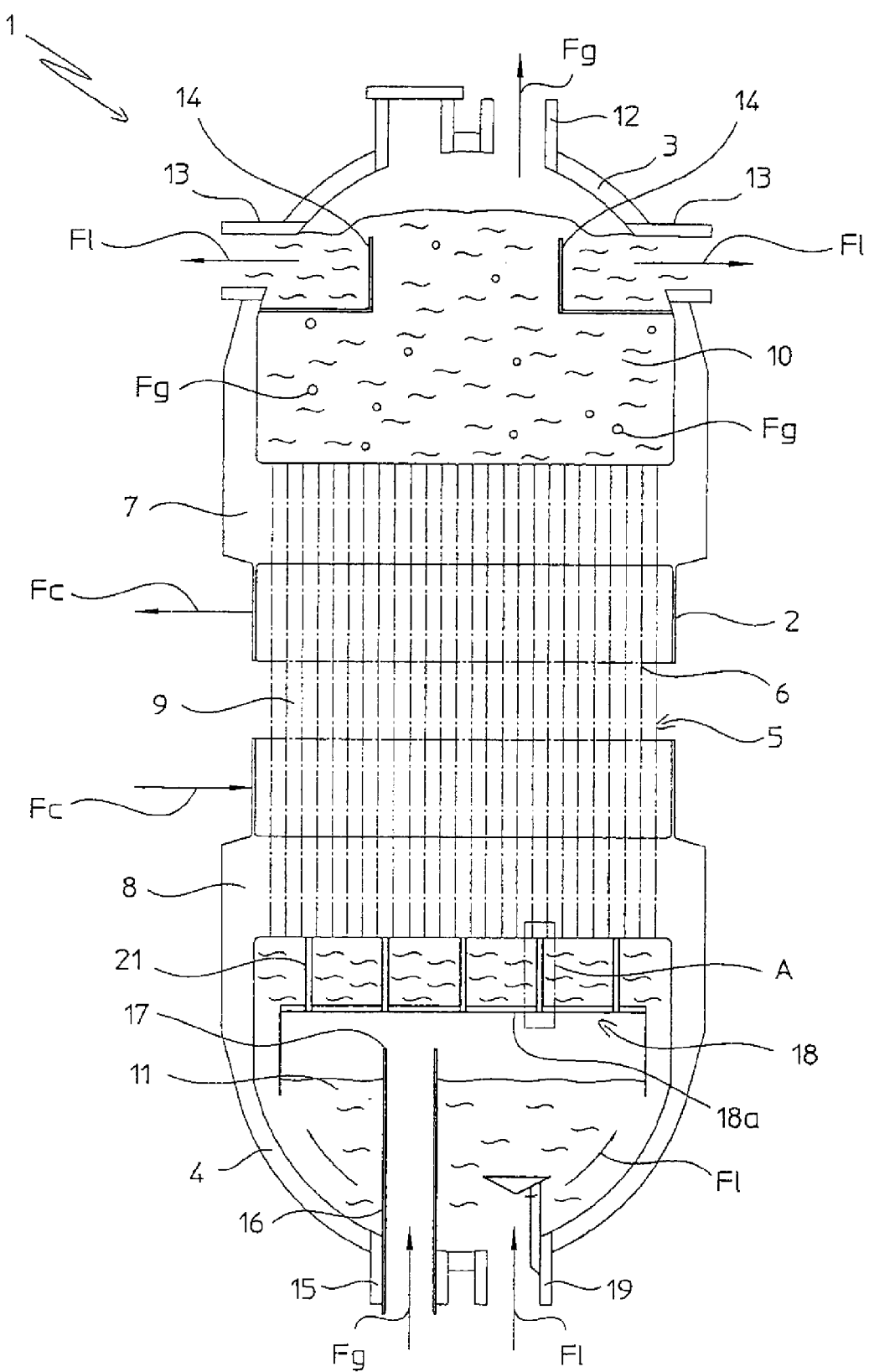
FIG. 1 shows a schematic view in longitudinal section of a condensation unit for carrying out the method according to the present invention.
Figure 2:
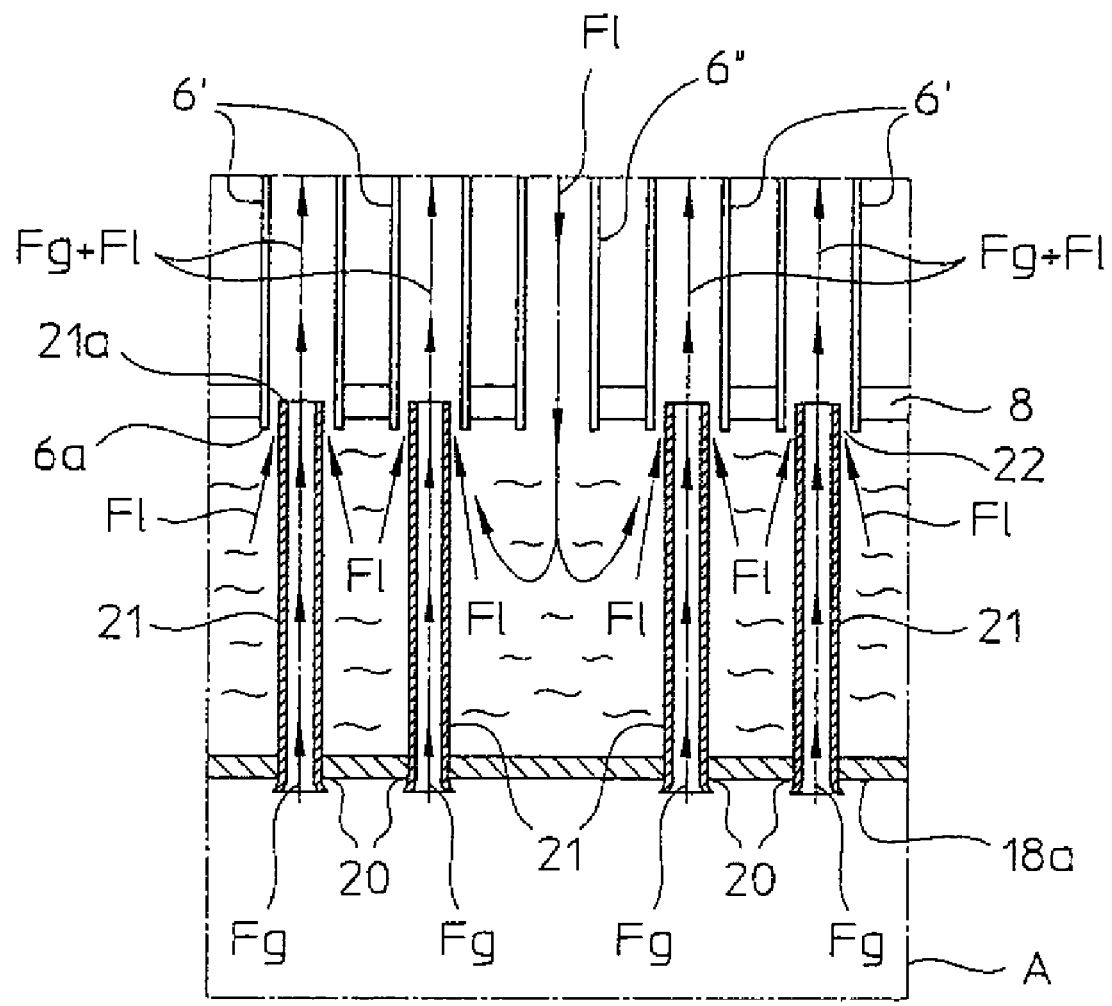
FIG. 2 shows a schematic view in longitudinal section of a detail of the condensation unit according to FIG. 1.

With reference to FIGS. 1 and 2, with 1 is globally indicated a condensation unit for carrying out the method according to the present invention comprising a cylindrical shell 2 closed at the opposed ends by an upper bottom 3 and a lower bottom 4, respectively.

In the shell 2 a tube bundle 5 is supported having a predetermined size, i.e. having a predetermined number of straight tubes 6 of predetermined length and diameter, said straight tubes 6 being supported by opposed upper and lower tube plates 7, 8, respectively. Said plates 7 and 8 separate the shell 2, which defines an intermediate portion 9 of the condensation unit, from the bottoms 3 and 4, which define an upper portion 10 and a lower portion 11 of the condensation unit 1, respectively.

Said portions 10 and 11 are reciprocally in fluid communication through the plurality of straight tubes 6 of the tube bundle 5. The tubes 6 are grouped in tubes 6' intended for carbamate condensation at their internal and in tubes 6" intended for recycle of a portion of the condensed gaseous compounds from the upper portion 10 to the lower portion 11 of the condensation unit 1.

It should be noted that said tube bundle 5 is in heat exchange relationship with a coolant, for example water, flowing outside the tubes 6 (shell side) and fed into the condensation unit and exiting therefrom through suitable openings and connecting means that are not shown as per se conventional.

The upper portion 10 of the condensation unit is provided with a first gas discharge opening 12, formed in the upper bottom 3 and with second openings 13 formed in the side part of the portion itself.

In said portion 10, and in proximity to said second openings 13, overflow devices 14 are provided, which are schematically illustrated by a baffle.

The lower portion 11 is provided with a first opening 15 to which passes a first duct 16 fastened thereto, for feeding the gases to be condensed, and a second opening 19 for feeding the liquid phase, as will be clear in the following description.

Said first duct 16 has a free end 17, located inside a gas distribution chamber 18, supported in a conventional manner inside said lower portion 11 of the condensation unit. The distribution chamber 18 comprises a perforated wall 18a provided proximate to the lower tube plate 8.

According to the present invention, and as better shown in the detail A of FIG. 2, the condensation unit 1 comprises a plurality of connecting ducts 21 extending from the gas distribution chamber 18 to the internal of the tubes 6' intended for condensation, so as to obtain a direct gas communication between said chamber and said tubes. For simplicity of presentation, in FIG. 1, ducts 21 are only randomly and schematically shown and do not reflect the actual number and position of such ducts represented in the detail of FIG. 2.

In particular, the connecting ducts 21 pass through and are fastened to openings 20 of the perforated wall 18a and have a free upper end 21a ending within and in proximity of a lower end 6a of the tubes 6' intended for condensation.

Preferably, the upper end 21a of the connecting ducts 21 has a diameter slightly smaller than the diameter of the lower end 6a of the tubes 6' intended for condensation, so that an annular space 22 is defined between ducts 21 and tubes 6' for the inlet thereto of the liquid phase.

With reference to the condensation unit 1 of FIGS. 1 and 2, it is now described an example of implementation of the carbamate condensation method according to the present invention. In these figures, Fg and Fl generally indicate the flows of the gaseous phase and of the liquid phase inside the condensation unit 1, respectively, while Fg+Fl indicates a mixed gaseous/liquid phase flowing within the tubes 6' intended for condensation. Moreover, Fc further schematically indicates the flow of a coolant fed to the condensation unit 1 and withdrawn therefrom.

With reference to FIG. 1, the volume of the condensation unit 1, schematically illustrated when in regular operation, is entirely taken up by the liquid phase, that is an aqueous solution comprising carbamate, ammonia and optionally urea, and by the gaseous phase, that is gaseous compounds comprising ammonia, carbon dioxide and generally water in the form of vapors.

Said gaseous compounds in a vapor phase come from a stripping unit (not shown) downstream a synthesis reactor (not shown) for the decomposition of carbamate and the ammonia and carbon dioxide stripping from the urea solution coming from the synthesis reactor. These compounds are fed into the condensation unit by the above said first feeding duct 16 and collected in the gas distribution chamber 18 within the lower portion 11.

At the same time, a flow comprising carbamate in aqueous solution coming from a urea recovery section (not shown), and optionally a solution comprising urea and unreacted substances coming from the synthesis reactor (not shown) and feed liquid ammonia, are fed in the lower portion 11 of the condensation unit 1 through the second opening 19.

Advantageously, according to the present method, the liquid phase and the gaseous phase are fed contemporaneously and independently within each of said tubes 6' intended for condensation, so that gas and liquid are first contacted and mixed for reaction and condensation of the gaseous reactants to carbamate in such tubes 6', only. In other words, there is no mixing of these two phases in the lower portion 11, between the gas distribution chamber 18 and the lower tube plate 8.

To this aim, said gaseous phase is made to flow from the distribution chamber 18 to the internal of the tubes 6' intended for condensation, in the proximity of their lower end 6a, through the connecting ducts 21; while the liquid phase flows from the second opening 19 around the gas distribution chamber 18 and enters the tubes 6' through the annular spaces 22 defined between ducts 21 and tubes 6'.

Inside said tube 6', the two phases are mixed together and ammonia, carbon dioxide and water first condensate and then ammonia reacts with carbon dioxide, thus forming carbamate.

This carbamate is added to the carbamate already present in the aqueous solution inside the condensation unit 1, obtaining in this way, at the outlet of the tubes 6', one carbamate solution possibly comprising also urea.

The carbamate solution flows in the upper portion 10, wherein a first part thereof is recycled to the lower portion 11 through the ducts 6", and a second part thereof exits the unit 1 through the openings 13 with a flow regulated by the overflow devices 14. The portion of solution exiting the unit 1 through the openings 13 is then sent to the synthesis reactor for the conversion into urea of the carbamate and ammonia therein contained.

It should be noted that the ducts 6" provide the circulation of the liquid phase inside the condensation unit 1, in particular from the upper portion 10 of the condensation unit 1 to its lower portion 11.

Thanks to the features of the present invention, it is possible to homogenously and uniformly distribute the gaseous compounds within all tubes 6' of the tube bundle 5 intended for condensation, avoiding the formation of undesired preferential paths of gas phase, thus exploiting the tube bundle 5 according to its design operation.

It follows that the condensation yield and the efficiency of the condensation unit 1 are substantially improved with respect to the prior art. In fact, it is now possible to carry out the carbamate condensation reaction within each of the tubes 6' intended for condensation at substantially the same operating conditions. This also positively affect the natural circulation of the liquid phase within the unit 1, which guarantees that the tubes 6' intended for condensation are always full of solution and contain a constant amount thereof and allows an optimal crossing speed through the tubes 6' to be maintained by the liquid phase to all advantage of the heat exchange between said liquid phase and the coolant flowing outside the tubes, and therefore of an effective condensation of the gaseous compounds.

Should any gaseous substance be still present in the upper portion 10, they will be vented from the condensation unit 1 through the opening 12 provided in the upper bottom 3.

The synthesis reactor, the stripping unit and the condensation unit 1 are all part of the so-called high-pressure synthesis loop of plant for the industrial production of urea. Such apparatuses do in fact operate substantially at the same pressure and are connected the one to the other in order to make possible the separation and recycle to the synthesis reactor of at least a portion of the unreacted substances contained in the urea solution coming out therefrom.

The above described carbamate condensation method and unit 1 for carrying out such a method are subject to modifications and changes.

Figure 3:
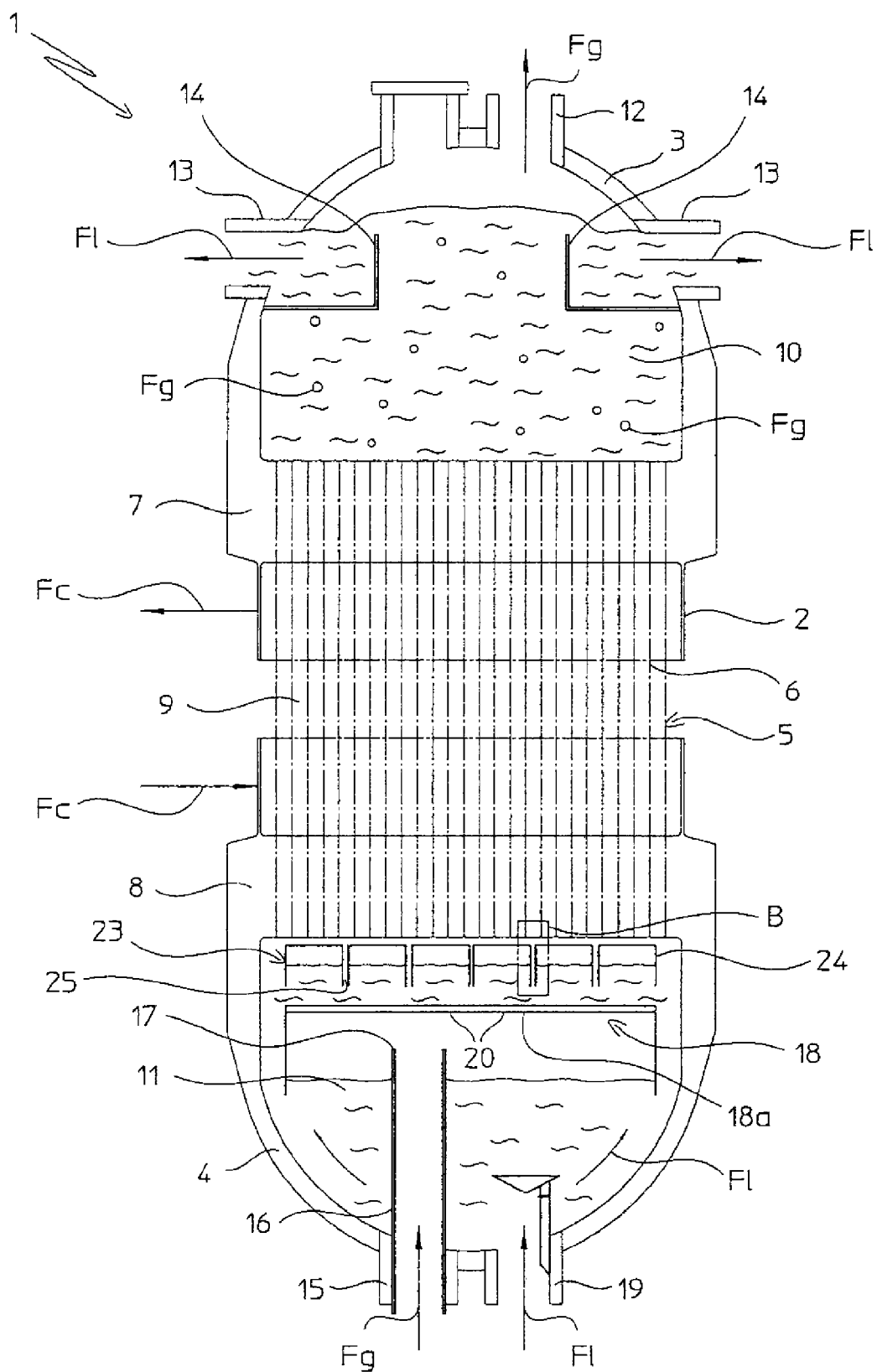
FIG. 3 shows schematic view in longitudinal section of a further embodiment of the condensation unit for carrying out the method according to the present invention.
Figure 4:
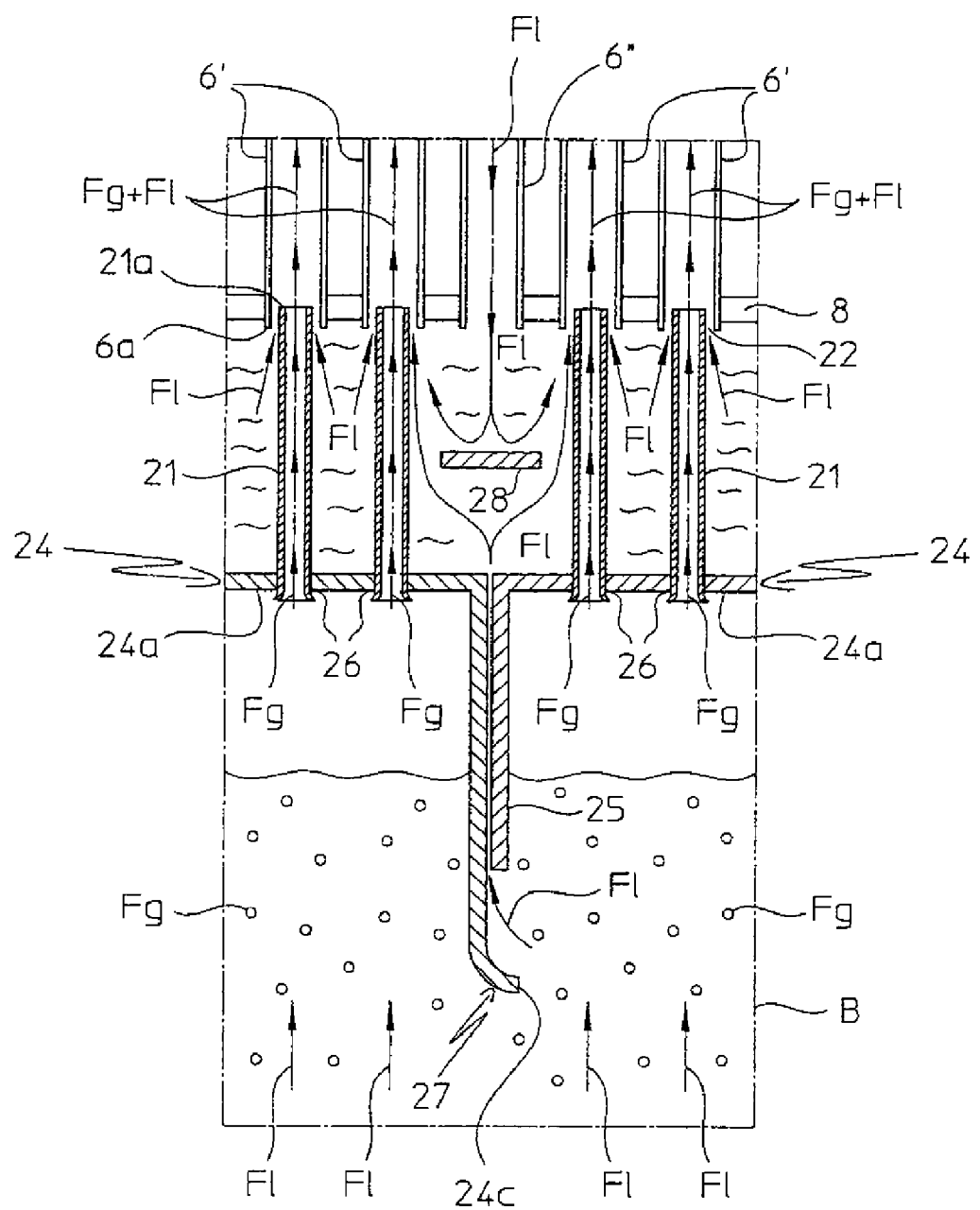
FIG. 4 shows a schematic view in longitudinal section of a detail of the condensation unit according to FIG. 3.

Thus, an alternative embodiment of the invention is for example shown with reference to FIGS. 3 and 4.

In this figures, the details of the condensation unit 1 that are structurally and functionally equivalent to those illustrated in FIGS. 1-2 will be indicated with the same reference numbers and will not be described any more.

According to this embodiment, the carbamate condensation unit 1 comprises a further gas distributor chamber, generally indicated by reference 23, supported in a conventional manner inside said lower portion 11 above the gas distribution chamber 18 and of substantially the same shape.

The further chamber 23 is advantageously divided in a plurality of sectors 24 (six in the example of FIG. 3), contiguous, but slighted separated the one from the other so as to define intermediate channels 25 for the passage of the liquid phase between the sectors 24.

The sectors 24 are closed at their top by a perforated wall 24a provided in the close proximity of the lower tube plate 8.

According to the present embodiment of the invention, and as better shown in the detail B of FIG. 4, the connecting ducts 21 now extend from the sectors 24 of the further gas distribution chamber 23 to the internal of the tubes 6' intended for condensation, so as to obtain a direct gas communication between said further chamber and said tubes. For simplicity of presentation, in FIG. 3, ducts 21 have not been shown.

In particular, the connecting ducts 21 pass through and are fastened to openings 26 of the sector perforated wall 24a and have the free upper end 21a ending within and in proximity of the lower end 6a of the tubes 6' intended for condensation.

With reference to the embodiment of FIGS. 3 and 4, the implementation of the carbamate condensation method according to the present invention substantially corresponds to that described with respect to FIGS. 1-2, with the exception that: the gaseous compounds leave the gas distribution chamber 18 trough the openings 20, are temporarily mixed with the liquid phase above such chamber 18 and are collected again in the sectors 24 of the further gas distribution chamber 23.

From here, the gaseous compounds are advantageously directly and independently fed within each of said tubes 6' intended for condensation, through the connecting ducts 21, where they mix for reaction and condensation to carbamate with the liquid phase contemporaneously entering such tubes 6' through the annular spaces 22, in heat exchange relationship with the coolant flowing outside the tube bundle 5.

Also in this case, there is no mixing of the two phases just below the lower tube plate 8, so that formation of gas preferential paths, i.e. uneven distribution of the gaseous phase, is prevented.

The presence of the intermediate channels 25 between adjacent sectors 24 for the passage thereinbetween of the liquid phase, advantageously allows an optimal distribution of the liquid phase above such sectors 24 before entering the tubes 6' intended for condensation.

The distance between adjacent sectors 24, i.e. the width of the channels 25, is chosen in a way to impede gaseous compounds to flow in the channels 25. To this aim, the carbamate condensation unit 1 preferably comprises gas deflecting means 27 associated to the channels 25.

In the example of FIGS. 3-4, the gas deflecting means 25 are advantageously obtained by providing the side walls 24b of the sectors 24 with different length and shape, so that once the sectors are arranged one beside the other, one of the two opposite side walls 24b of adjacent sectors 24 is longer then the other and its free end 24c is curved towards and extend over the shorter side wall.

Preferably, the carbamate condensation unit 1 further comprises a plurality of deflecting baffles 28 arranged in the lower portion 11, between the sectors 24 and the lower tube plate 8, below said tubes 6" intended for recycle of the liquid phase. By doing so, it is possible to better control the flow direction of the liquid phase coming downwardly from the tubes 6" and the liquid phase coming upwardly through the channels 25, to all advantage of the natural circulation of the liquid phase within the unit 1.

According to another embodiment of the present invention, the sectors 24 are preferably in gas communication the ones with the others by means of tubular connectors (not shown) that advantageously allows an improved and more homogeneous gas distribution of the gaseous compounds within the further gas distribution chamber 23. Moreover, the presence of such tubular connectors also permits to strengthen the structure of the chamber 23

With respect to the sectors 24, it should be noted that also the gas distribution chamber 18 can be structured as the further gas distribution chamber 23, i.e. divided in a plurality of contiguous sectors. In this case, means (not shown as being per se conventional) are provided between the duct 16 and the different sectors, for uniformly feeding to the latter the gaseous compounds.

The embodiments of FIGS. 1-4 are particularly advantageous for the revamping of pre-existing condensation units of the submerged type or even of the film type.

In the latter units, the liquid phase is made to flow for gravity inside the tubes of a tube bundle as a film of liquid in co-current with the gaseous compounds to be condensed.

In general, in pre-existing condensation units it is not possible neither economically convenient to make structural modifications to the same, in particular to the shell.

Advantageously, thanks to the present invention, the pre-existing carbamate condensation unit is provided in its lower portion with gas distribution chamber(s) and connecting ducts for feeding, contemporaneously and independently, the gaseous phase and the liquid phase within each of the tubes of the heat exchange tube bundle intended for condensation, without the need of intervening onto the existing structure of the shell and of the bottoms. By doing so, the efficiency and the condensation yield of the unit are drastically increased.

Advantageously, the carbamate condensation method of the present invention can also be applied to submerged condensation units of the type disclosed in WO 02/34382, wherein the predetermined number of tubes intended for carbamate condensation corresponds to the overall number of tubes of the tube bundle and the recycle of the liquid phase is obtained through a structurally independent duct.

In this respect, it should be noted that the number and the arrangement of the tubes intended for condensation and of the tubes intended for recycling of a portion of the condensed compounds given in the FIGS. 1-4 are merely by way of non-limiting and explanatory example, and can be modified depending on the required operating conditions or structure of the unit.

The invention thus conceived is susceptible to further embodiments and modifications all of which are within the capabilities of the man skilled in the art and, as such, fall within the scope of protection of the invention itself, as defined by the following claims.

The invention claimed is:

1. A carbamate condensation unit of the submerged type for carbamate condensation of a carbon dioxide/ammonia gaseous phase in a liquid phase, comprising:
    a heat exchange tube bundle having a predetermined number of first tubes intended for carbamate condensation at their interior and a predetermined number of second tubes intended for circulation of said liquid phase inside said condensation unit from an upper portion of the condensation unit to a lower portion of the condensation unit;
    a gas distribution chamber for collecting said gas phase fed to said condensation unit; and
    a plurality of connecting ducts extending from said gas distribution chamber to the interior of said first tubes intended for condensation, so as to obtain a direct gas communication between said chamber and said first tubes.

2. The condensation unit according to claim 1, wherein said connecting ducts have a free upper end ending within and in proximity of a lower end of said tubes intended for condensation.

3. The condensation unit according to claim 2, wherein said upper end of the connecting ducts has a diameter smaller than the diameter of said lower end of the tubes intended for condensation, so that an annular space is defined between said ducts and said tubes for the inlet thereto of the liquid phase.

4. The carbamate condensation unit of the submerged type for carbamate condensation of a carbon dioxide/ammonia gaseous phase in a liquid phase, comprising:
    a heat exchange tube bundle having a predetermined number of tubes intended for carbamate condensation at their interior a gas distribution chamber for collecting said gas phase fed to said condensation unit arranged below said tube bundle;
    a further gas distribution chamber arranged between said gas distribution chamber and said tube bundle for collecting said gas phase coming from said gas distribution chamber; and
    a plurality of connecting ducts extending from said further gas distribution chamber to the interior said tubes intended for condensation, so as to obtain a direct gas communication between said further chamber and said tubes.

5. The condensation unit according to claim 4, wherein said connecting ducts have a free upper end ending within and in proximity of a lower end of said tubes intended for condensation.

6. The condensation unit according to claim 5, wherein said upper end of the connecting ducts has a diameter smaller than the diameter of said lower end of the tubes intended for condensation, so that an annular space is defined between said ducts and said tubes for the inlet thereto of the liquid phase.

7. The condensation unit according to claim 4, wherein said further gas distribution chamber is divided in a plurality of sectors, contiguous and separated the one from the other so as to define intermediate channels for the passage of said liquid phase between said sectors.

8. The condensation unit according to claim 7, wherein it further comprises gas deflecting means associated to said intermediate channels.

9. The condensation unit according to claim 8, wherein said gas deflecting means are obtained by providing said sectors with side walls of different length and shape, so that once said sectors are arranged one beside the other within said unit, one of the two opposite side walls of adjacent sectors is longer then the other and has a free end curved towards and extending to the opposite shorter side wall.

10. The condensation unit according to claim 7, wherein said sectors in gas communication the ones with the others by means of tubular connectors.

11. The condensation unit according to claim 4, wherein it further comprises at least one deflecting baffle arranged between said gas distributing chamber and said tube bundle, below at least one tube of the tube bundle intended for recycling said liquid phase.

12. The condensation unit according to claim 4, wherein it further comprises at least one deflecting baffle arranged between said further gas distribution chamber and said tube bundle, below at least one tube of the tube bundle intended for recycling said liquid phase.

* * * * *